(12) United States Patent
Savaide et al.

(10) Patent No.: US 7,550,137 B2
(45) Date of Patent: Jun. 23, 2009

(54) METHOD AND COMPOSITION FOR WAVING AND STRAIGHTENING HAIR

(75) Inventors: Andrew Savaide, Norwalk, CT (US); Rushi Tasker, Trumbull, CT (US); Wesley A. Evans, Old Tappan, NJ (US)

(73) Assignee: Zotos International, Inc., Darien, CT (US)

( * ) Notice: Subject to any disclaimer, the term of this patent is extended or adjusted under 35 U.S.C. 154(b) by 810 days.

(21) Appl. No.: 11/125,061

(22) Filed: May 9, 2005

(65) Prior Publication Data

US 2006/0251599 A1    Nov. 9, 2006

(51) Int. Cl.
*A61Q 5/04*     (2006.01)
(52) U.S. Cl. ............... 424/70.5; 424/70.2; 132/202; 132/203
(58) Field of Classification Search ............ None
See application file for complete search history.

(56) References Cited

U.S. PATENT DOCUMENTS

| 5,338,540 A | * | 8/1994 | Lee et al. ............... 424/70.4 |
| 5,350,572 A | * | 9/1994 | Savaides et al. ......... 424/70.5 |
| 5,775,342 A |   | 7/1998 | Hohenstein et al. |
| 6,378,530 B1 | * | 4/2002 | Rezvani et al. ............ 132/205 |

* cited by examiner

*Primary Examiner*—Jyothsna A Venkat
(74) *Attorney, Agent, or Firm*—Melvin I. Stoltz

(57) ABSTRACT

An improved process and composition for straightening or waving hair is achieved combining ammonium bisulfite and ethanolamine sulfite in a single mixture which is maintained at a pH of between about 6.5 and 8.0. By employing the present invention, long lasting, waved or straightened hair is attained. Furthermore, using the hair waving/straightening composition and method of the present invention, the desired waving and/or straightening of hair fiber is achieved in a single step, without the need for a separate application of an oxidizing or neutralizing agent.

9 Claims, No Drawings

METHOD AND COMPOSITION FOR WAVING AND STRAIGHTENING HAIR

TECHNICAL FIELD

This invention relates to the art of waving and/or straightening hair, and more particularly, to new formulations and processes for waving or straightening hair which provide long-lasting, durable waved/straightened hair while also eliminating the need for a separate oxidation or neutralization step.

BACKGROUND ART

The waving or straightening of hair is a well established and well developed art in which substantial attention has been directed to improve the present level of technology. Although substantial changes have occurred throughout the last decades, various problems continue to plague the industry in spite of numerous attempts to reduce or eliminate these problems.

In order to best understand the present state of the art and the problems existing therein, it is important to reiterate that hair fibers are composed of a unique protein called "keratin" which is distinguished by the fact that it contains a very significant amount of an amino acid (cystine) which contains the element sulfur in addition to the elements nitrogen, oxygen, carbon and hydrogen. In the natural biosynthesis of hair, the element sulfur covalently links intra or inter polypeptide chains (K) through two sulfur atoms (S—S) to give keratin protein (K—S—S—K). Only by chemical action can this covalent linkage be broken.

Since these disulfide bonds are relatively strong bonds and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for the cold permanent waving of hair. Typically, these prior art systems treat the hair with reducing agents which break the disulfide (cystine) linkage in the hair, while the hair is wound around a curling rod.

In general, permanent hair waving is usually carried out by subjecting the hair to reagents containing a free —SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules.

In addition to the waving of hair using the organic thiol compounds, substantial effort has been expended in waving or straightening hair using aqueous alcoholic ammonia and non-alkali metal bisulfites and sulfites without an oxidative fixative treatment. The chemistry employed for waving and straightening hair using bisulfite and sulfite compounds is very different from the use of thiols.

In this regard, the chemical reaction (1) of bisulfite with SS bonds of hair, as shown below, can produce equal bunte salts ($KSSO_3$) and Cysteine residues (KSH). In addition, hydrogen bonds and salt linkages in hair are also cleaved with the bisulfite solutions. The prior known processes use acidic hydrogen peroxide solutions shown by chemical reaction (2) to reform the disulfide SS bonds from the cleaved cysteine residues.

$$KSSK + HSO_3 \rightarrow KSSO_3 + KSH \quad (1)$$

$$KSH + \tfrac{1}{2}H_2O_2 \rightarrow KSSK + H_2O \quad (2)$$

In these reactions, the acidic hydrogen peroxide has no effect on the bunte salt and therefore no disulfide bonds are reformed. This implies that a maximum of 50% of the original SS broken bonds may not be recovered and will result into hair damage and weak curl formation. The composition disclosed in U.S. Pat. No. 5,775,342 uses premixed alkaline hydrogen peroxide solutions of 1.80-2.20% by weight and pH of 8.50-9.20 to cleave the bunte salt shown in chemical reaction (3) to form SS disulfide bonds. Thus the alkaline hydrogen peroxide solution produces a more efficient "lock in" set, however with excessive hair surface damage and hair color lightening due to oxidation of melanin. Furthermore higher oxidation products in hair can occur under these conditions such as cysteic acid in chemical reaction (4)

$$KSSO_3 + OH \rightarrow KSH + SO_4 + H_2O_2 - KSSK + H_2O \quad (3)$$

$$KSSK + H_2O_2 \rightarrow KSO_3 + H_2O \quad (4)$$

Although numerous prior art products have been developed based upon the use of bisulfites and sulfites, these prior art systems have been found to be deficient in satisfying all of the needs and desires of users. In particular, these prior art compositions suffer from slow diffusion of actives into the cortex of hair fibers and slow reaction rates with hair. These factors typically result in poor overall wave performance. Furthermore, the prior art compositions typically bleach the natural color of hair, produce excessive hair damage, and leave an unpleasant malodor residue in hair.

Therefore, it is a principal object of the present invention to provide a composition and a method of use for waving or straightening hair fibers which is capable of imparting a longer-lasting hair set, while completely eliminating the need for applying an oxidizing or neutralizing agent.

Another object of the present invention is to provide a hair waving/straightening composition and method of use having the characteristic features described above which is capable of improving the physical properties of the treated hair, such as a shine, luster, softness, manageability, hair body and thickness.

Another object of the present invention is to provide a hair waving/straightening composition and method of use having the characteristic features described above which substantially reduces or eliminates damage to the hair fibers while also substantially reducing or eliminating bleaching of the natural color of hair.

Another object of the present invention is to provide a hair waving/straightening composition and method of use having the characteristic features described above which virtually eliminates any residual unpleasant malodor on hair fibers, as well as providing an efficient system where actives rapidly diffuse into the hair fibers while providing rapid reaction rates with the hair fibers.

Other and more specific objects will in part be obvious and will in part appear hereinafter.

DETAILED DESCRIPTION

By employing the present invention, the prior art difficulties, drawbacks, and limitations have been overcome and long lasting, waved or straightened hair is attained. Using the hair waving/straightening composition and method of the present invention, the desired waving and/or straightening of hair fiber is achieved in a single step, without the need for a separate application of an oxidizing or neutralizing agent.

In accordance with the present invention, the process and composition for straightening or waving hair comprises the combination of ammonium bisulfite and ethanolamine sulfite in a single mixture which is maintained at a pH of between about 6.70 and 7.70. In addition, the optimum ratio of the ammonium bisulfite to the ethanolamine sulfite in the reducing mixture combination is 9.00%:4.00% or a ratio of 1.22:1 at a pH of 6.90. In the preferred embodiment, the composition does not require any buffering agents and is applied to the hair as a liquid or as a non-aerosol foam.

In order to provide a full and complete disclosure of the present invention, the preferred formulation for the hair straightening/waving composition of the present invention is fully detailed in Table I. As is apparent from a review of Table I, the preferred ingredients for the compositions of the present invention are provided, along with the preferred range of each ingredient. However, it is to be understood that variations of these ingredients can be implemented without departing from the overall scope of this invention. In this way, by employing formulations constructed from the teaching of Table 1, a hair straightening/waving composition is realized which can be employed to attain the desired results in a single application step.

In Tables II and III, two alternate, specific formulations made in accordance with the present invention are provided. In Table II, the specific, preferred composition for normal hair is fully detailed while Table III defines the preferred formulation for use with color treated hair.

TABLE 1

Hair Straightening/Waving Composition

| Ingredient | Amount (% by weight/total weight) |
|---|---|
| Hydroxyethylcellulose | 0.05-3.00 |
| Ammonium Bisulfite | 7-11 |
| Ethanolamine Sulfite | 1-5 |
| Urea | 1-3 |
| Propylene Glycol | 0.5-1 |
| Glycerol | 0.5-1 |
| Isopropanol | 0.1-1 |
| Ethoxydiglycol | 0.1-0.5 |
| Quaternium-75 | 0.1-1 |
| Cinannamidopropyldimmonium Chloride | 0.025-0.05 |
| Hydrolyzed keratin PG-Propyl Methylsilanediol | 0.1-0.5 |
| Perfume | 0.4-.090 |
| Nonionic Surfactant | 1.5-4.0 |
| Alkali Agent | QS to pH |

TABLE II

Preferred Hair Straightening/Waving For Normal Hair

| Ingredient | Amount (% by weight/total weight) |
|---|---|
| Hydroxyethylcellulose | 0.20 |
| Ammonium Bisulfite | 20.25 |
| Ethanolamine Sulfite | 6.75 |
| Urea | 2.5 |
| Propylene Glycol | 1 |
| Glycerol | 1 |
| Isopropanol | 1 |
| Ethoxydiglycol | 0.2 |
| Quaternium-75 | 0.2 |
| Cinannamidopropyldimmonium Chloride | 0.001 |
| Hydrolyzed keratin PG-Propyl Methylsilanediol | 0.001 |
| Perfume | 0.7 |

TABLE II-continued

Preferred Hair Straightening/Waving For Normal Hair

| Ingredient | Amount (% by weight/total weight) |
|---|---|
| Polysorbate 20 | 1.5 |
| Ammonium Hydroxide (28%) | 3.5 |
| RO Water | 61.20 |

TABLE III

Preferred Hair Straightening/Waving For Color Treated Hair

| Ingredient | Amount (% by weight/total weight) |
|---|---|
| Hydroxyethylcellulose | 0.30 |
| Ammonium Bisulfite | 16 |
| Ethanolamine Sulfite | 5 |
| Urea | 1.5 |
| Propylene Glycol | 0.5 |
| Glycerol | 0.5 |
| Ethoxydiglycol | 0.2 |
| Quaternium-75 | 0.2 |
| Cinannamidopropyldimmonium Chloride | 0.001 |
| Hydrolyzed keratin PG-Propyl Methylsilanediol | 0.001 |
| Perfume | 0.7 |
| Polysorbate 20 | 1.5 |
| Ammonium Hydroxide (28%) | 2.5 |
| RO Water q.s. to 100% | 69.0 |

Throughout this disclosure, chemical compounds are referred to using their generic names or using the designations adopted by the Cosmetic Toiletry and Fragrance Association (CTFA). In addition, in certain circumstances, trade names are used parenthetically.

As detailed above, formulations constructed from the teaching of the present invention can be configured for being dispensed either as a liquid or as a non-aerosol foam. In one preferred embodiment, in order to attain a foam product, the formulation of the present invention is retained in a desired container on which a non-aerosol finger pump foamer is mounted, preferably with an extended dispensing tip of one inch to 3 inches in length. By employing this dispensing system, a high quality foam is produced by precise mixing of liquid and air per stroke which ranges between about 14.8 and 18.8 mm, or 0.75 and 1.5 g. Using this construction, highly effective and efficacious results have been realized.

Although any desired non-aerosol producing finger pump foamers can be employed for dispensing the formulations of the present invention, it has been found that the "F2 Finger Pump Foamers" provide the best results. These foamers are produced by Airspray International B.V. of the Netherlands.

The composition of the present invention can be employed for waving hair or for straightening hair. In this regard, regardless of the particular results desired, the compositions detailed herein can be employed in order to attain the particular desired style, with the application process or method being altered for achieving the desired result. In particular, it has been found that waving of hair fibers is most effectively achieved by applying the composition of the present invention to dampened, prewrapped hair on which rods, rollers, curlers, or other tools have been secured.

In the preferred application method for achieving waved hair fibers, the composition of the present invention is applied to the hair fibers, as detailed above, and allowed to dissipate into the hair fibers within five minutes. Thereafter, the hair is capped and processed at room temperature, or under a preheated dryer at a temperature ranging between about 40° C. and 55° C. for a period of time ranging between about 15 and 60 minutes. Thereafter, the hair is rinsed for about five to ten minutes, depending on the length of hair and the tools are removed from the hair. No neutralization is required and the hair is styled to achieve the desired visual appearance.

By employing the process and composition of the present invention, good, durable waved hair sets are realized by minimizing "bunte salt" residue formation and providing good recovery of cystine SS bonds in the hair. Furthermore, the integrity of the hair is maintained without requiring neutralization oxidant mixtures, such as hydrogen peroxide.

It is believed that the removal of "bunte salt" occurs under the operation of two theoretical models or chemical reactions. One of these models/reactions is due to charge destabilization reaction (5), while the second is the intermolecular reactions occurring at temperatures ranging between about 180° C. and 210° C. between the helical chains, as defined below in reactions (6) and (7).

$$KSSKO_3 + Charge(-) \rightarrow KSH \quad (5)$$

$$KSSO_3 + K_2SH + Heat \rightarrow KSSK_2 + HSO_3 \quad (6)$$

$$KSSO_3 + K_2SSO_3 + K_3SSO_3 + Heat \rightarrow KSSK_2 + K_2SSK_3 + KSSK_3 \quad (7)$$

As discussed above, the composition of the present invention can be employed as either a liquid or as a foam. In this regard, however, it has been found that the use of the present invention as a foam offers many advantages. These advantages include constant degassing of the product/packaging head space, which results in a cleaner, fresher applied product.

Furthermore, the foam product can be applied to dry or pre-wet hair before or after wrapping of the hair fibers. In addition, by applying the foam to the hair fibers, the foam composition does not drip off of the hair fibers, as often occurs in the liquid form. Contact between the composition and the scalp is minimized and no protection of the scalp by cotton along the hair line is required. Finally, the use of foam provides an positive indicator of a precise location where the product has been applied to the hair, thereby enabling the product to be applied to all hair sections without missing any section or overlapping areas of application.

It has also been found that the performance of the compositions of the present invention are enhanced when the compositions are applied to the hair in the foam form. It is believed that this enhanced performance is due to surface tension effects and flux/capillary models which enhance the diffusion of the foam product into the hair fibers to be greater than is attained with the compositions in the liquid form.

EXAMPLES

In order to substantiate the versatility and substantial hair enhancements achieved by employing the hair waving/straightening composition of the present invention, as well as by employing the single step application method of this invention, the following examples are presented. In the following disclosure, the universal applicability of this invention is fully detailed, along with the ability of the hair waving/straightening composition of the present invention to achieve the desired results, while completely eliminating the need for a separate application of an oxidizing or neutralizing agent. It is to be understood, however, that these examples are intended as a teaching of the best mode for carrying out the present invention and are not intended to limit, in any manner, the breath of this discovery.

In demonstrating the efficacy of the hair waving composition of the present invention, various tests were conducted on hair fibers to which the compositions of the present invention were applied using the method detailed above. In general, normal hair fibers of 7 inches in length were wrapped on 16 mm rods and treated with the preferred composition defined in Table II at a ratio of 3:1 (hair:liquid). The composition was allowed to remain on the hair fibers for between about 30 and 40 minutes under a preheated dryer at a temperature ranging between about 40° C. and 49° C. Thereafter, the hair was rinsed with warm water for about seven minutes. When this application method was completed, various tests were performed on the hair fibers, as detailed below in the Tables IV, V, and VI.

One test conducted to demonstrate the efficacy of the hair waving composition of the present invention was the Tress Strand Method. By employing the Tress Strand Method, the amount of curvature of the hair fiber attained by the waving lotion is able to be determined. In using the Tress Strand Method, the length of each hair tress is measured prior to the application of the wave of lotion to the hair tress. After the treatment, as detailed above, the length of the resulting tresses are measured, along with the number of crests. The curvature is determined from the following formula:

Curvature=(initial length of hair tress)×(number of crests)/length of treated hair tress An acceptable curl will have a curvature value from about 3 to 10. Curvature values of less than 3.0 are cosmetically unacceptable.

In addition, in the following tables, the tensile strength of the hair fibers treated using the hair waving composition of the present invention was determined, as well as a 20% index, which is a measure of hair damage. Furthermore, bunte salt formation and removal was also evaluated and compared with permanent wave solutions employing neutralization. Finally, an amino acid analysis of the treated hair was also performed with the resulting information provided below.

TABLE IV

TSM AND TENSILE STRENGTH STUDIES

| | Normal Hair | | | Colored Hair | |
|---|---|---|---|---|---|
| Processing Time | 10% Index | 20% Index | Curvature | 20% Index | Curvature |
| 30 Minutes | 0.855 | 0.824 | 3.05 | 0.812 | 3.46 |
| 30 Minutes + Neutralization | 0.849 | 0.848 | 3.10 | 0.820 | 3.25 |
| 40 Minutes | 0.837 | 0.810 | 3.10 | 0.808 | 3.58 |
| 40 Minutes + Neutralization | 0.837 | 0.835 | 3.10 | 0.805 | 3.57 |
| 60 Minutes | | 0.824 | 3.15 | — | — |
| 7 Hours | | 0.754 | 4.28 | 0.776 | 4.3 |
| 24 Hours | | 0.779 | 4.50 | 0.749 | 4.8 |

TABLE V

BUNTE SALT FORMATION AND REMOVAL WITH
BISCARBONATE AND ALKALINE PERM TREATMENT

| | 20% Index | | |
|---|---|---|---|
| Treatment | One-Step (No. Neut) | BisCarbonate + Neut. | Alkaline Perm + Neut. |
| 1× | 0.785 | 0.918 | |
| 2× | 0.706 | 0.830 | |
| 4× | 0.699 | — | |
| 4× + BisCarbonate | | 0.819 | |
| 4× + Alkaline Perm | | | 0.764 |

TABLE VI

AMINO ACID ANALYSIS OF TREATED HAIR

NMOLES/GRAM HAIR

| SAMPLE | ½ Cystine | Cysteic | Cysteine | Total | % Recovery |
|---|---|---|---|---|---|
| Virgin Hair | 107,494 | 5,093 | None Detect. | 112,587 | |
| 1× | 92,247 | 8,120 | None Detect. | 100,367 | 89.15 |
| 2× | 86,952 | 8,337 | None Detect. | 85,289 | 84.64 |
| 2×! Sis Carb. Neutralizer | 103,651 | 4,851 | None Detect. | 108,502 | 96.37 |

As is evident from the foregoing disclosure and the test data provided herein, the hair waving/straightening composition of the present invention is capable of providing a highly desirable wave in a simple, easily employed, one step process, without requiring the use of a neutralizing agent. As is evident from the foregoing disclosure, the resulting waved hair is equivalent to or better than results attained using conventional formulations and processes, while eliminating extra steps and unnecessary chemical exposure.

It will thus be seen that the objects set forth above, among those made apparent from the proceeding description, are efficiently attained and, since certain changes may be made in carrying out the above method and in the composition set forth without departing from the scope of the invention, it intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

Having described our invention, what we claim as now and desire to secure by Letters Patent is:

The invention claimed is:

1. A hair waving/straightening composition consisting of
A. from 0.05% to 3.0% by weight based upon the weight of the entire composition of hydroxyethylcellulose;
B. from 7% to 11% by weight based upon the weight of the entire composition of ammonium bisulfite;
C. from 1% to 5% by weight based upon the weight of the entire composition of ethanolamine sulfite;
D. from 1% to 3% by weight based on the weight of the entire composition of the urea;
E. from 1.5% to 4% by weight based upon the weight of the entire composition of a nonionic surfactant;
F. an alkali agent in sufficient quantities to obtain the desired pH
G. from 0.5% to 1% by weight based upon the weight of the entire composition of propylene glycol;
H. from 0.5% to 1% by weight based upon the weight of the entire composition of glycerol;
I. from 0.1% to 1% by weight based upon the weight of the entire composition of isopropanol;
J. from 0.1% to 0.5% by weight based upon the weight of the entire composition of ethoxydiglycol;
K. from 0.1% to 1% by weight based upon the weight of the entire composition of quaternium-75;
L. from 0.025% to 0.05% by weight based upon the weight of the entire composition of cinannamidopropyldimmonium chloride;
M. from 0.1% to 0.5% by weight based upon the weight of the entire composition of hydrolyzed keratin PG-propyl methylsilanediol; and
N. from 0.4% to 0.9% by weight based upon the weight of the entire composition of at least one perfume.

2. The hair waving/straightening composition defined in claim 1, wherein said composition is formulated as comprising one selected from the group consisting of liquids and foams.

3. A system for waving or straightening hair comprising:
A. a composition; according to claim 1 and
B. a container constructed for retaining said composition therein, with said container incorporating a non-aerosol finger pump foam dispenser;
whereby said composition is dispensed from said container as a foam product.

4. The hair waving/straightening system defined in claim 3, wherein said non-aerosol finger pump foam dispenser is further defined as comprising an F2 finger pump foamer incorporating an extended dispenser tip.

5. The hair waving/straightening system defined in claim 4, wherein the foam output from said container for each stroke ranges between about 14.8 and 18.8 mm or 0.75 and 1.5 g.

6. A method for waving hair comprising the steps of
A. winding the hair fibers onto tools selected from the group consisting of rods, rollers, and curlers;
B. dampenning the prewrapped hair fibers;
C. applying a waving composition to the dampened, hair wound on the tools, said waving composition consisting of:
A. from 0.05% to 3.0% by weight based upon the weight of the entire composition of hydroxyethylcellulose;
B. from 7% to 11% by weight based upon the weight of the entire composition of ammonium bisulfite;
C. from 1% to 5% by weight based upon the weight of the entire composition of ethanolamine sulfite;
D. from 1% to 3% by weight based on the weight of the entire composition of the urea;
E. from 1.5% to 4% by weight based upon the weight of the entire composition of a nonionic surfactant;
F. an alkali agent in sufficient quantities to obtain the desired pH
G. from 0.5% to 1% by weight based upon the weight of the entire composition of propylene glycol;
H. from 0.5% to 1% by weight based upon the weight of the entire composition of glycerol;
I. from 0.1% to 1% by weight based upon the weight of the entire composition of isopropanol;
J. from 0.1% to 0.5% by weight based upon the weight of the entire composition of ethoxydiglycol;

K. from 0.1% to 1% by weight based upon the weight of the entire composition of quaternium-75;

L. from 0.025% to 0.05% by weight based upon the weight of the entire composition of cinannamidopropyldimmonium chloride;

M. from 0.1% to 0.5% by weight based upon the weight of the entire composition of hydrolyzed keratin PG-propyl methylsilanediol; and N. between about 0.4% and 0.9% by weight based upon the weight of the entire composition of at least one perfume D. allowing the waving composition to dissipate into the hair fibers within five minutes;

E. capping the hair and allowing the waving lotion to process for a period of time ranging between about 15 and 60 minutes;

F. removing the tools from the hair and rinsing the hair for about five minutes; and G. styling the hair to achieve the desired appearance;
whereby waved hair is achieved without requiring the use of neutralization/oxidant compositions.

7. The method for waving hair defined in claim 6, wherein the capped hair is allowed to process at room temperature.

8. The method for waving hair defined in claim 6, wherein the capped hair is processed under a preheated hair dryer maintained at a temperature ranging between about 49° C. and 55° C.

9. The method defined in claim 6, wherein said composition is further defined as being retained in a container having a non-aerosol finger pump foam dispenser and said composition is dispensed and applied to the hair as a foam.

* * * * *

UNITED STATES PATENT AND TRADEMARK OFFICE
CERTIFICATE OF CORRECTION

| | |
|---|---|
| PATENT NO. | : 7,550,137 B2 |
| APPLICATION NO. | : 11/125061 |
| DATED | : June 23, 2009 |
| INVENTOR(S) | : Andrew Savaides, Rushi Tasker and Wesley A. Evans |

It is certified that error appears in the above-identified patent and that said Letters Patent is hereby corrected as shown below:

On the Title Page, Item (75)
Please change the first named inventor from "Andrew Savaide" to
-- Andrew Savaides --

Signed and Sealed this

First Day of September, 2009

David J. Kappos
*Director of the United States Patent and Trademark Office*